(12) United States Patent
Joung

(10) Patent No.: US 7,579,600 B2
(45) Date of Patent: Aug. 25, 2009

(54) PRECLINICAL SPECT SYSTEM USING MULTI-PINHOLE COLLIMATION

(75) Inventor: Jinhun Joung, Algonquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 229 days.

(21) Appl. No.: 11/478,886

(22) Filed: Jun. 30, 2006

(65) Prior Publication Data

US 2008/0001088 A1 Jan. 3, 2008

(51) Int. Cl.
*G21K 1/02* (2006.01)
(52) U.S. Cl. .................................. 250/363.1
(58) Field of Classification Search . 250/363.01–363.1; 378/98.6–98.8
See application file for complete search history.

(56) References Cited

U.S. PATENT DOCUMENTS

| | | | |
|---|---|---|---|
| 7,166,846 B2 | 1/2007 | Engdahl et al. | |
| 7,262,415 B2 * | 8/2007 | Crosetto | 250/363.05 |
| 2005/0056788 A1 * | 3/2005 | Juni | 250/363.04 |
| 2005/0078797 A1 * | 4/2005 | Danielsson et al. | 378/145 |

OTHER PUBLICATIONS

Smith et al., "Design of High Sensitivity, High Resolution Compact Single Photon Imaging Devices for Small Animal and Dedicated Breast Imaging," Nov. 2001, IEEE, Nuclear Science Symposium Conference Record, vol. 3, pp. 1592-1596.*

Zeniya et al., "3D image reconstruction using complete data in pinhole SPECT," 2003, IEEE Nuclear Science Symposium Conference Record, vol. 3, pp. 2100-2102.*

Lackas et al., T-SPECT: A Novel Imaging Technique for Small Animal Research, IEEE Transactions on Nuclear Science, vol. 52, No. 1, Feb. 2005, pp. 181-187.

* cited by examiner

*Primary Examiner*—David P Porta
*Assistant Examiner*—Kiho Kim

(57) ABSTRACT

A preclinical nuclear imaging detector system, including a gantry and one or more detector assemblies, each including a scintillator configured to interact with radiation emanating from a target test object being imaged and at least one pinhole collimator, having one or more pinhole apertures formed therein. The pinhole collimator is disposed between the target object and the scintillator, wherein a distance between the pinhole aperture and the scintillator is selected as a function of the number of pinhole apertures provided in the collimator and to optimize one of sensitivity or spatial resolution, such that the one or more pinhole apertures collectively project a unitary minified radiation image of the target object onto the scintillator. Further, one or more photosensors are optically coupled to the scintillator to receive interaction events from the scintillator.

20 Claims, 9 Drawing Sheets

PRECLINICAL SPECT SYSTEM USING MULTI-PINHOLE COLLIMATION

FIELD OF THE INVENTION

The instant invention generally relates to nuclear medicine, and systems for obtaining nuclear medical images of interest. In particular, the instant invention relates to a novel detector configuration for preclinical single photon imaging including single photon emission computed tomography (SPECT) or planar imaging

BACKGROUND OF THE INVENTION

Nuclear imaging is a unique specialty wherein radiation is used to acquire images that show the function and anatomy of organs, bones or tissues of the body. Radiopharmaceuticals are introduced into the subject, either by injection or ingestion, and are attracted to specific organs, bones or tissues of interest. Such radiopharmaceuticals produce gamma photon emissions that emanate from the body. One or more detectors are used to detect the emitted gamma photons, and the information collected from the detector(s) is processed to calculate the position of origin of the emitted photon from the source (i.e., the body organ or tissue under study). The accumulation of a large number of emitted gamma positions allows an image of the organ or tissue under study to be displayed.

In conventional nuclear imaging arrangements, collimators are used in a wide variety of equipment in which it is desired to permit only beams of radiation emanating along a particular path to pass a selected point or plane. Collimators are frequently used in nuclear imagers to ensure that only radiation beams passing along a direct path from the known radiation source strike the detector thereby minimizing detection of beams of scattered or secondary radiation.

Particularly in nuclear imagers used for preclinical analysis or for non-destructive evaluation procedures, it is important that only radiation emanating from a known source and passing along a direct path from that source be detected and processed by the imaging equipment. If the detector is struck by undesired radiation such as that passing along non-direct paths to the detector, performance of the imaging system can be degraded.

Two principal types of collimators have been used in nuclear imaging. The predominant type of collimation is the parallel-hole collimator. This type of collimator contains hundreds of parallel holes drilled or etched into a very dense material such as lead. The parallel-hole collimator accepts only photons traveling perpendicular to the scintillator surface, and produces a planar image of the same size as the source object. In general, the resolution of the parallel-hole collimator increases as the holes are made smaller in diameter and longer in length.

The conventional pinhole collimator typically is cone-shaped and has a single small hole drilled in the center of the collimator material. The pinhole collimator generates a magnified image of an object in accordance with its acceptance angle, and is primarily used in studying small organs such as the thyroid or localized objects such as a joint. The pinhole collimator must be placed at a very small distance from the object being imaged in order to achieve acceptable image quality. Pinhole collimators offer the benefit of high magnification of a single object, but lose resolution and sensitivity as the field of view (FOV) gets wider and the object is farther away from the pinhole.

U.S. Pat. No. 7,166,846, assigned to the same assignee herein and incorporated herein by reference in its entirety, discloses a multi-pinhole collimator nuclear medical imaging detector that divides a target object space into many non-overlapping areas and projects a minified image of each area onto a segmented detector, where each segment functions as an independent detector or imaging cell.

Other known types of collimators include the slant-hole collimator, converging and diverging collimators, and the fan beam collimator. The slant-hole collimator is a variation of the parallel-hole collimator but with all holes slanted at a specific angle. This type of collimator is positioned close to the body and produces an oblique view for better visualization of an organ whose line of sight may be partially blocked by other parts of the body. The converging collimator has holes that are not parallel but instead are focused toward the organ, with the focal point being located in the center of the field of view. The image appears larger at the face of the scintillator using a converging collimator. A diverging collimator results by reversing the direction of the converging collimator. The diverging collimator is typically used to enlarge the FOV, such as would be necessary with a portable camera having a small scintillator. The fan beam collimator is typically used with a rectangular camera head to image smaller organs. The holes are parallel when viewed from one direction and converge when viewed from another direction. The fan beam collimator allows the maximum surface of the crystal to be used to capture imaging data. In most applications, the choice of collimation represents a trade-off between the size of the FOV and the sensitivity and spatial resolution required to properly visualize the target object or organ.

Collimators are positioned to substantially absorb the undesired radiation before it reaches the detector. The collimator includes (or is manufactured from) a relatively high atomic number material and the collimator is positioned so that undesired radiation strikes the body of the collimator and is absorbed before being able to strike the detector. In a typical detector system the collimator includes barriers associated with the detector and located in the direction of the radiation source. An example exists in radiation imaging systems used for medical diagnosis which use a small point source of radiation to expose the patient under examination. The radiation passes through the patient and strikes a radiation detector that is oppositely positioned.

Conventional single photon imaging systems with parallel-hole collimation use large area (on the order of 2000 cm$^2$) monolithic scintillation detectors, and typically have an intrinsic spatial resolution of approximately 3.5 mm FWHM (Full Width Half Maximum). Such detectors are made either of sodium iodide crystals doped with thallium (NaI(Tl)), or cesium iodide (CsI). Scintillations within the NaI crystal caused by absorption of a gamma photon within the crystal, result in the emission of a number of light photons from the crystal. The scintillations are detected by an array of photomultiplier tubes (PMTs) in close optical coupling to the crystal surface.

The intrinsic spatial resolution is primarily determined by the size of the PMTs. The design of the parallel-hole collimator (i.e., the length and diameter of the collimator holes) fixes the system resolution, and represents a trade-off between sensitivity (i.e., the number of detected gamma rays) and spatial resolution (i.e., sharpness of the image) of the imaged target object. The system spatial resolution is a quadrature sum of the geometric resolution of the collimator and the intrinsic resolution of the camera. In most clinical imaging studies, the predominant spatial resolution achieved is determined by the geometric resolution of the collimator, and thus there has not been a strong incentive to increase the intrinsic spatial resolution of the gamma camera.

Conventional commercial gamma cameras are designed to minimize cost by using the largest possible size PMTs, and thus achieve an intrinsic spatial resolution of about 3.5 mm FWHM. However, recent detector technology has enabled the design of small gamma cameras with intrinsic spatial resolution of less than 1 mm FWHM. Thus, there exists a need in the art for improvements in collimator technology to take advantage of such increased intrinsic spatial resolution in the development of new commercial gamma cameras.

In the instance of SPECT scanning, a subject (patient) is infused with a radioactive substance that emits radioactive or gamma rays. Conventionally, a gamma camera includes a transducer to receive the gamma rays and record an image therefrom. In order for the image to be a true representation of the subject being investigated, a collimator having collimating apertures is positioned between the transducer and the subject to screen out all of the radioactive rays except those directed along a straight line through the collimating apertures between a particular part of the subject and a corresponding particular part of the transducer. Traditionally, the collimator is made of a radiation opaque material such as lead, and collimating apertures have been formed therein by various means such as drilling holes therethrough.

In conventional SPECT system designs, lead collimator gamma cameras have been supported on gantries that rotate the camera head through an angular range of one hundred eighty or three hundred sixty degrees around the patient. One drawback associated with this requirement however, is that such gantry systems are relatively expensive subsystems of the diagnostic tool because they must be capable of providing rapid rotation of the large and heavy camera heads through very precise orbits about the patient. Further, rotating gantries require a large degree of space for the actual unit as well as for full operational ability. This is especially problematic with preclinical SPECT wherein lab space limitations are more prevalent. As a result, one object of the present invention is to accommodate the use of space and money-saving simplified gantries, without sacrificing image quality.

SUMMARY OF THE INVENTION

In general, the invention features a preclinical nuclear imaging detector system, comprising a gantry and one or more detector assemblies. The gantry is optionally fixed and configured for securing the one or more detector assemblies substantially about an axis to thereby describe a portion of a detector perimeter. The one or more detector assemblies each comprise a scintillator configured to interact with radiation emanating from a target object being imaged and at least one pinhole collimator, having one or more pinhole apertures formed therein. The pinhole collimator is disposed between the target object and the scintillator, wherein a distance between the pinhole aperture and the scintillator is selected as a function of the number of pinhole apertures provided in the collimator, such that the one or more pinhole apertures collectively project a unitary minified radiation image of the target object onto the scintillator. Further, one or more photosensors are optically coupled to the scintillator to receive interaction events from the scintillator.

In one embodiment of the instant invention, the imaging detector system has a knife-edge pinhole collimator aperture. In another embodiment, the imaging detector system has a keel-edge pinhole collimator aperture.

In another embodiment, the imaging detector system has a perimeter that is a portion of an ellipse. In other embodiments, the imaging detector system has a perimeter that is a portion of a polygon. In still other embodiments, the imaging detector system has a perimeter that is a portion of a rectangle.

In still another embodiment, the detector assemblies form a substantially contiguous array disposed about a perimeter. In yet another embodiment, at least one or more detector assemblies have a pinhole plate, the adjustable pinhole plate is positionable relative to the scintillator and along an axis that is perpendicular to a plane of the scintillator. In yet still another embodiment, the pinhole collimator has a plurality of walls in slidable engagement with one another to allow the pinhole collimator to be positioned relative to the scintillator. In a further embodiment, the collimator has a plurality of walls disposed and slidable with respect to one another. In a yet further embodiment, the walls include a friction reducing element therebetween.

Generally, the instant invention features a method of performing a preclinical scan of a test subject employing a preclinical nuclear imaging detector system. The preclinical nuclear imaging detector system therefore comprises a gantry and one or more detector assemblies. The gantry is optionally fixed and configured for securing the one or more detector assemblies substantially about an axis to thereby describe a portion of a detector perimeter. The one or more detector assemblies each comprise a scintillator configured to interact with radiation emanating from a target object being imaged and at least one pinhole collimator, having one or more pinhole apertures formed therein. The pinhole collimator is disposed between the target object and the scintillator, wherein a distance between the pinhole aperture and the scintillator is selected as a function of the number of pinhole apertures provided in the collimator, such that the one or more pinhole apertures collectively project a unitary minified radiation image of the target object onto the scintillator. Further, one or more photosensors are optically coupled to the scintillator to receive interaction events from the scintillator. The method includes positioning a test subject with respect to the one or more detector assemblies, positioning the pinhole aperture with respect to the scintillator, then obtaining image data.

In another embodiment, a method of performing a preclinical scan of a test subject employs a preclinical nuclear imaging detector system including using a pinhole aperture that is positionable to effect a desired spatial resolution. In yet another embodiment, the method of performing a preclinical scan of a test subject employs a preclinical nuclear imaging detector system having a pinhole aperture that is positionable to effect a desired spatial sensitivity.

In still another embodiment, a method of performing a preclinical scan of a test subject employs a preclinical nuclear imaging detector system according to the instant invention including using a plurality of detectors configured to describe a portion of a perimeter. In yet still another embodiment, a method of performing a preclinical scan of a test subject employs a preclinical nuclear imaging detector system including using slidable collimators to adjust one of distance d and/or focal length f.

In other embodiments, a method of performing a preclinical scan of a test subject employs a preclinical nuclear imaging detector system including adjusting the distance d between the pinhole aperture and the subject between 100 mm and 300 mm. In yet other embodiments, a method of performing a preclinical scan of a test subject employing a preclinical nuclear imaging detector system includes adjusting distance d between the pinhole aperture and the subject between 125 mm and 225 mm. In still other embodiments, the method of performing a preclinical scan of a test subject employing a preclinical nuclear imaging detector system includes adjusting the distance d between the pinhole aperture and the subject to 125 mm. In yet still other embodiments, a method of performing a preclinical scan of a test subject employing a preclinical nuclear imaging detector system includes adjusting the distance d between the pinhole aperture and the subject to 225 mm.

Examples of the main features of this invention have thus been outlined rather broadly in order that the detailed description thereof that follows may be better understood, and in order that the contribution to the art may be better appreciated. There are, of course, additional features of the invention that will be described hereinafter and which will also form the subject of the claims appended hereto.

BRIEF DESCRIPTION OF THE DRAWINGS

The invention is pointed out with particularity in the claims. However, the above and further advantages of this invention may be better understood by referring to the following description taken in conjunction with the accompanying drawings, in which:

DETAILED DESCRIPTION OF EXEMPLARY EMBODIMENTS

Figure 1:
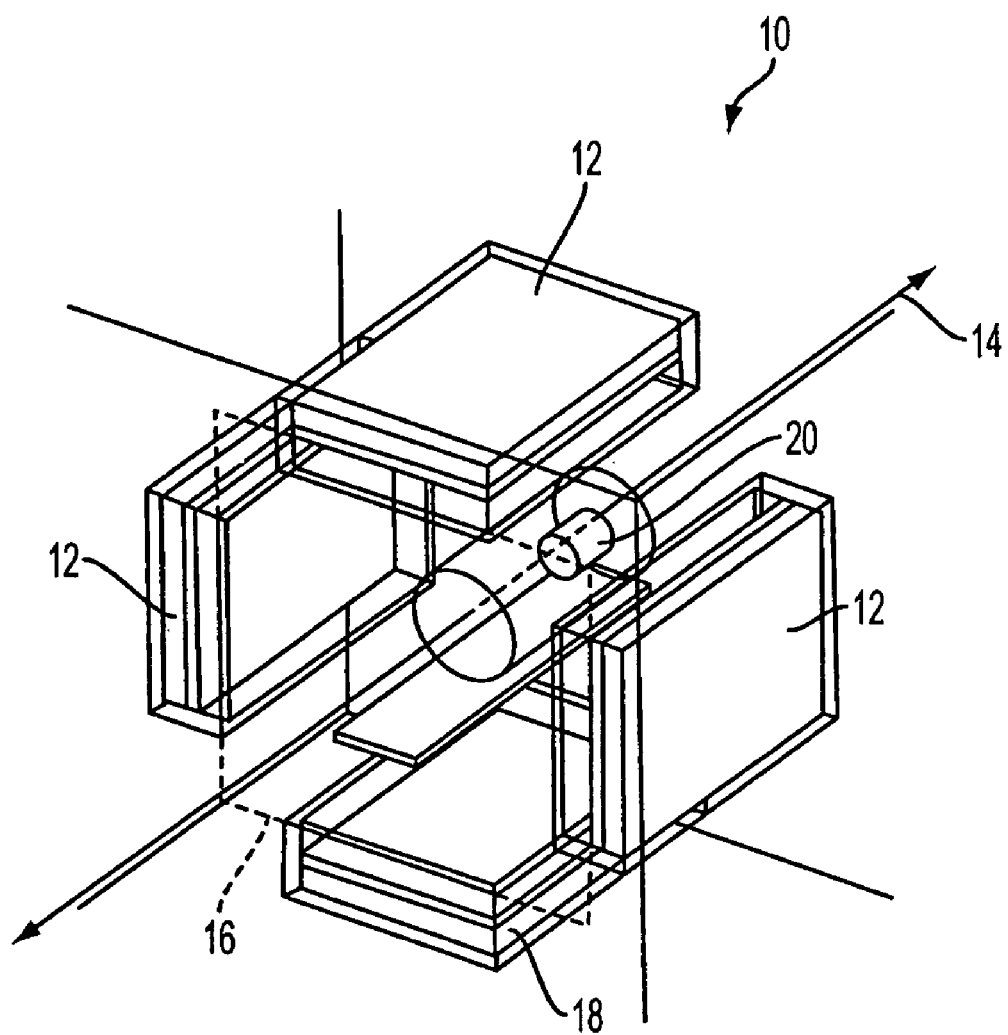
FIG. 1 is a schematic perspective view of a preclinical nuclear imaging detector system according to the instant invention.
Figure 5:
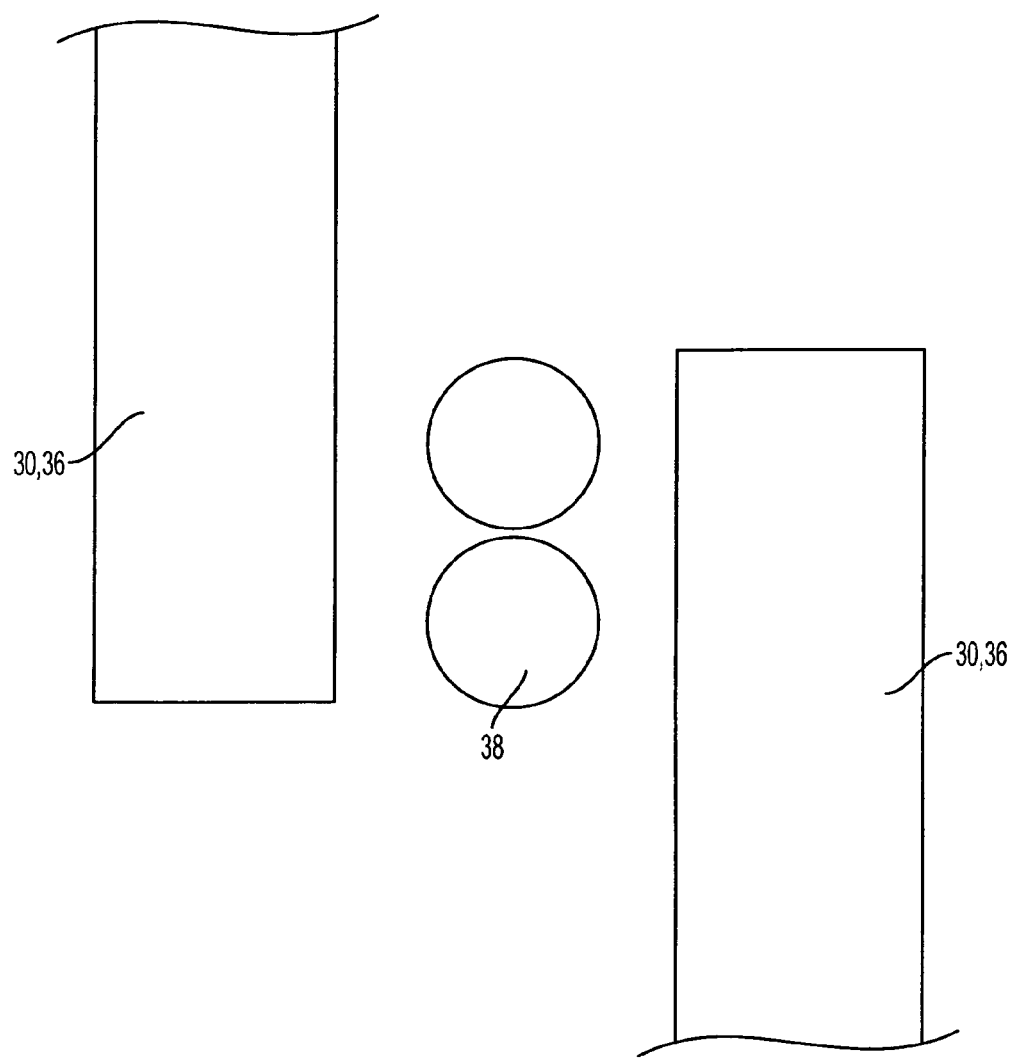
FIG. 5 is a close-up schematic illustration of a slide assembly for use with one of collimator walls and/or septa according to the instant invention.
Figure 6:
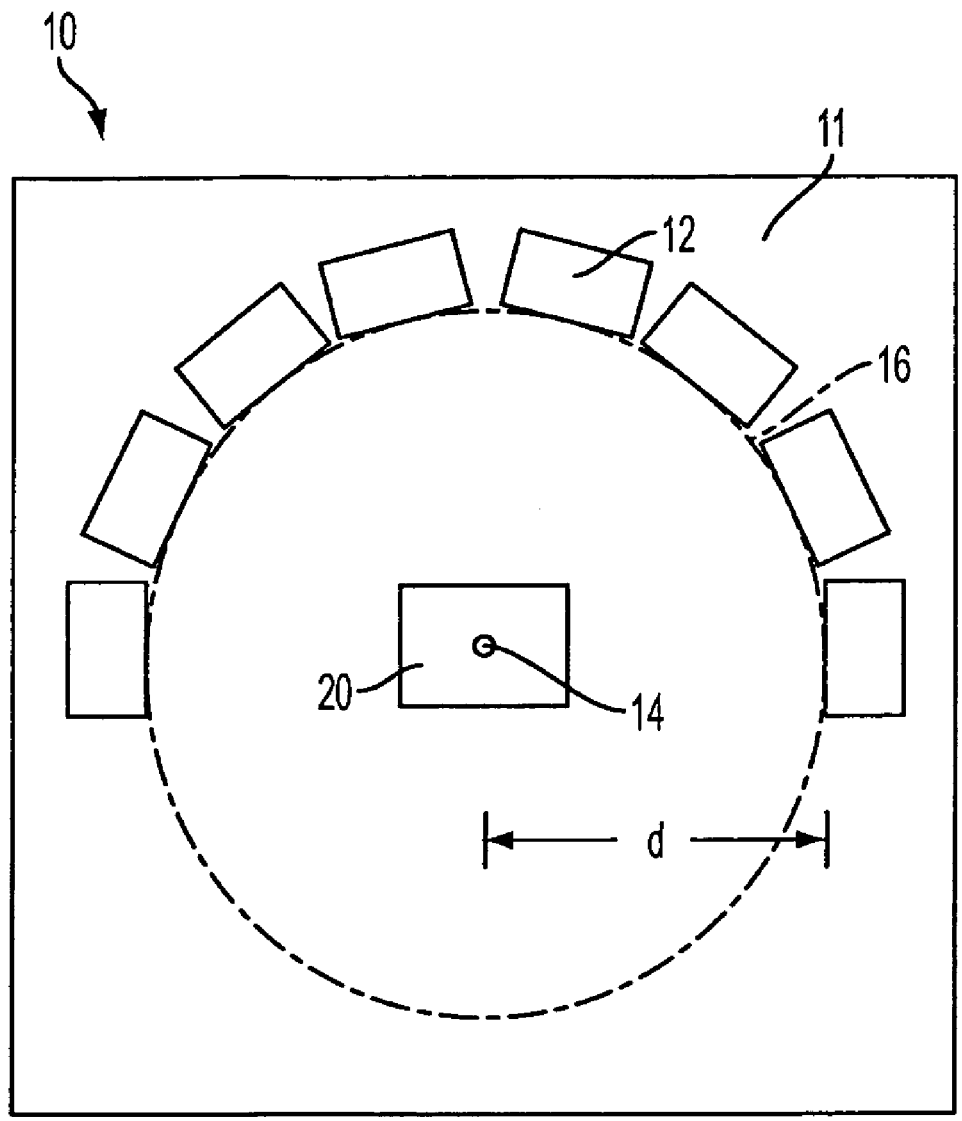
FIG. 6 is a schematic illustration of a preclinical nuclear imaging detector system comprising a plurality of detector assemblies disposed about and substantially defining a portion of a perimeter according the instant invention.

Referring now to the figures, FIGS. 1 and 6 disclose example embodiments of preclinical nuclear imaging detector systems according to the instant invention. The detectors of FIG. 1 are generally disposed in a rectangular or square configuration, whereas the detectors of FIG. 6 are generally disposed in an arcuate configuration. Generally, a preclinical nuclear imaging detector system 10 comprises one or more detector assemblies 12 secured to a gantry and/or support structure 11. Detector assemblies 12 are radially disposed about an axis 14 to thereby describe a perimeter 16 or a portion thereof and are optionally fixed relative to gantry and/or support structure 11. In the embodiment illustrated in FIG. 1, preclinical nuclear imaging detector system 10 further includes an object table 18 which is further shown supporting object 20, e.g., a phantom or test object such as a laboratory animal. Referring now to FIGS. 2 to 5, detector assembly 12 is shown as comprising a scintillator 22, at least one photosensor 26 optically coupled to said scintillator 22, and at least one collimator 24, which is preferably a pinhole collimator, and more preferably, a multi-pinhole collimator. For example, collimator 24 can be of a type disclosed and described in U.S. patent application Ser. No. 10/881,674 filed 30 Jun. 2004 and assigned to the same assignee herein, which application is incorporated herein by reference in its entirety.

Figure 2:
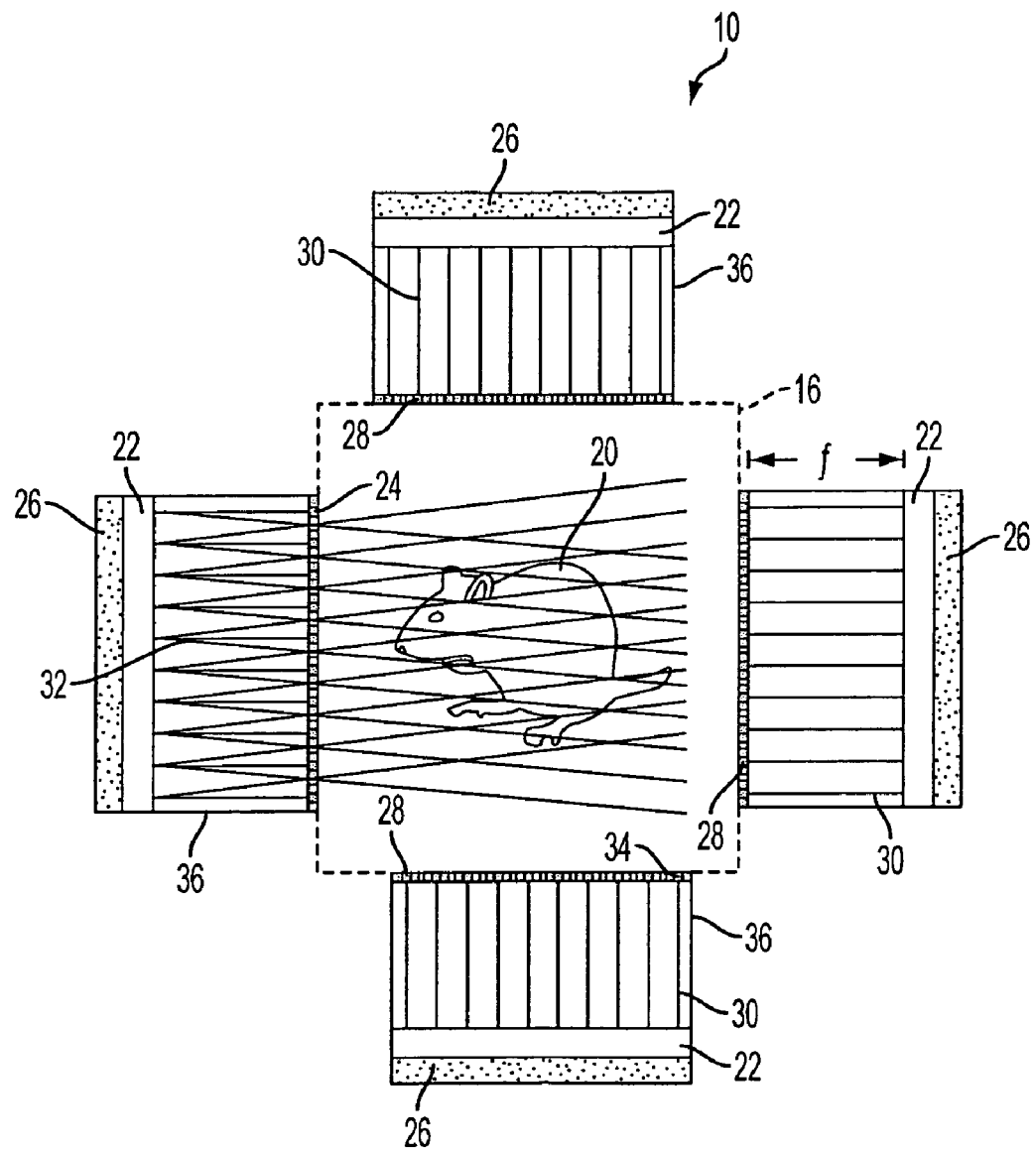
FIG. 2 is a schematic cross-sectional view of a preclinical nuclear imaging detector system according to the instant invention further illustrating a test subject.

As shown in FIG. 2, collimator 24 comprises a multi-pinhole collimator spaced apart from scintillator 22 by a focal length f such that the one or more pinhole apertures 28 collectively project a unitary minified radiation image of the subject 20 onto the scintillator 22. Also, at least one photosensor 26 is optically coupled to the scintillator 22 to receive interaction events from the scintillator 22.

Figure 3:
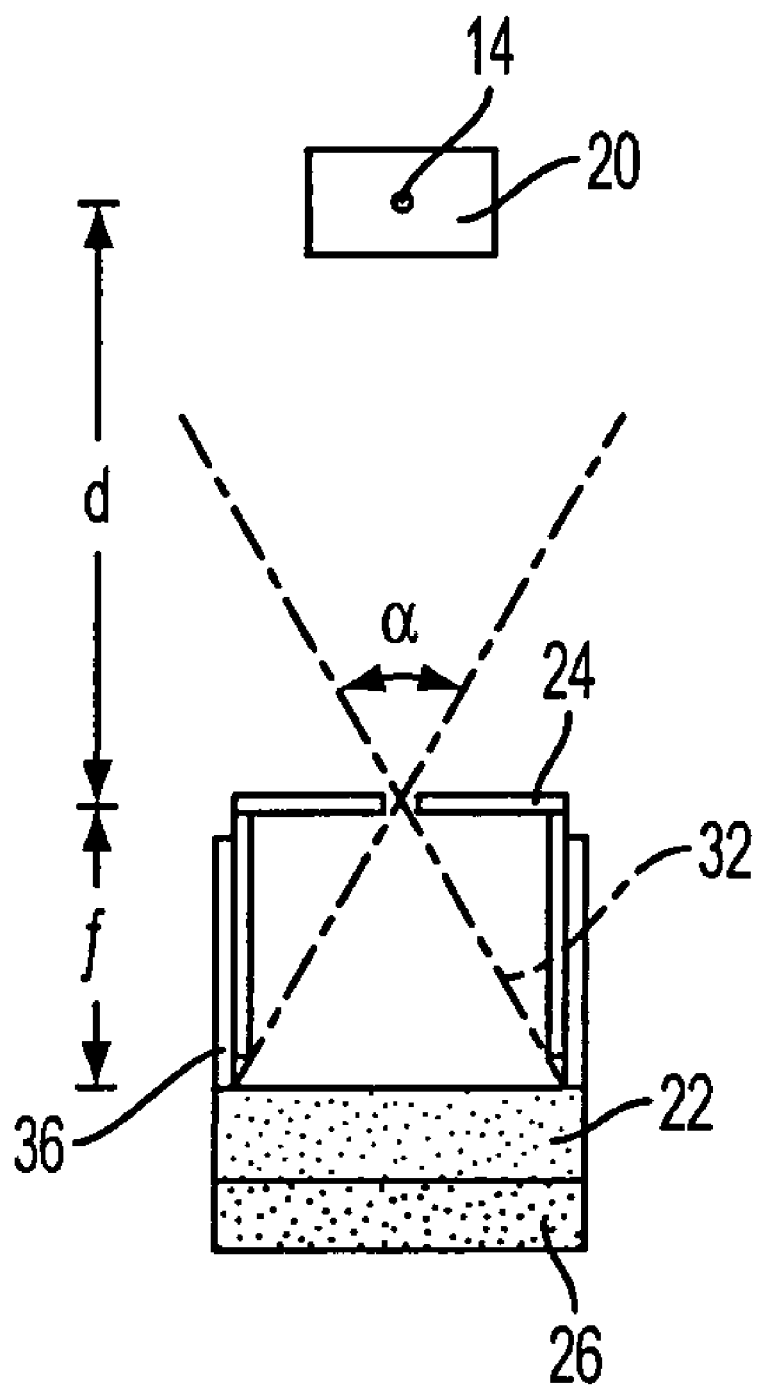
FIG. 3 is a schematic cross-sectional view of a detector assembly according to the instant invention wherein a pinhole aperture is disposed at a first distance f from a scintillator.
Figure 4:
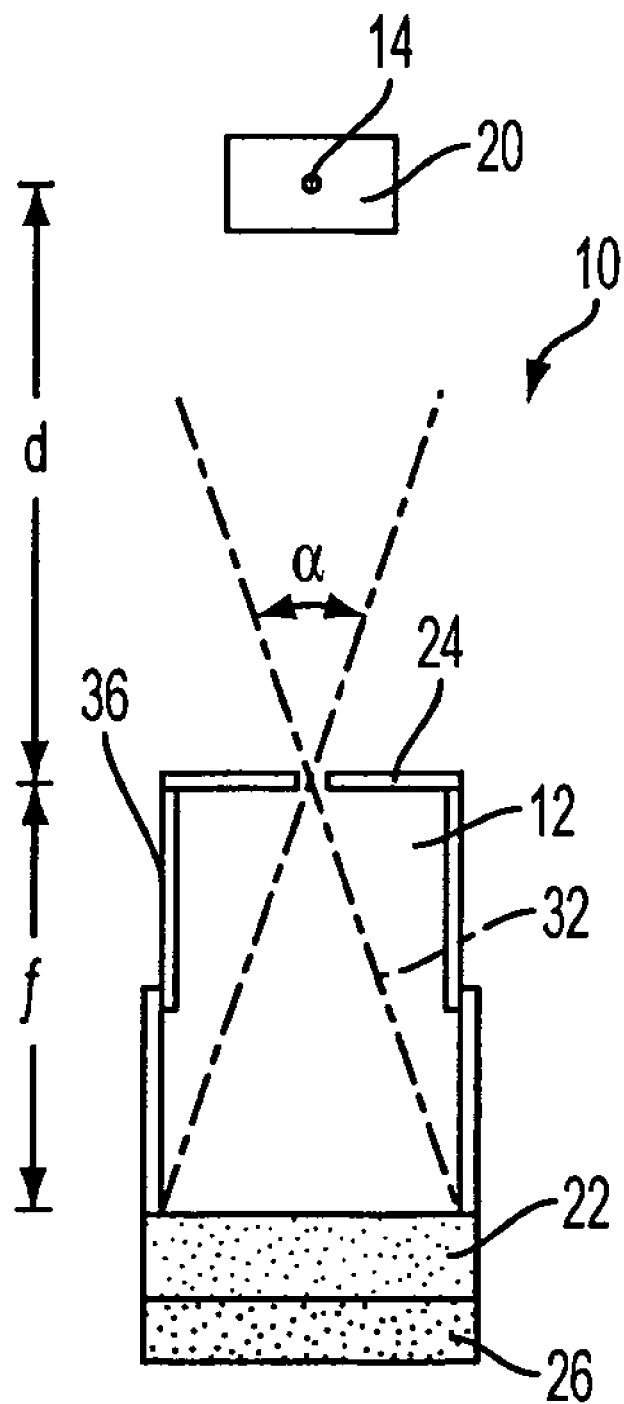
FIG. 4 is a schematic cross-sectional view of a detector assembly according to the instant invention wherein pinhole a aperture is disposed at a second distance f from a scintillator.
Figure 7:
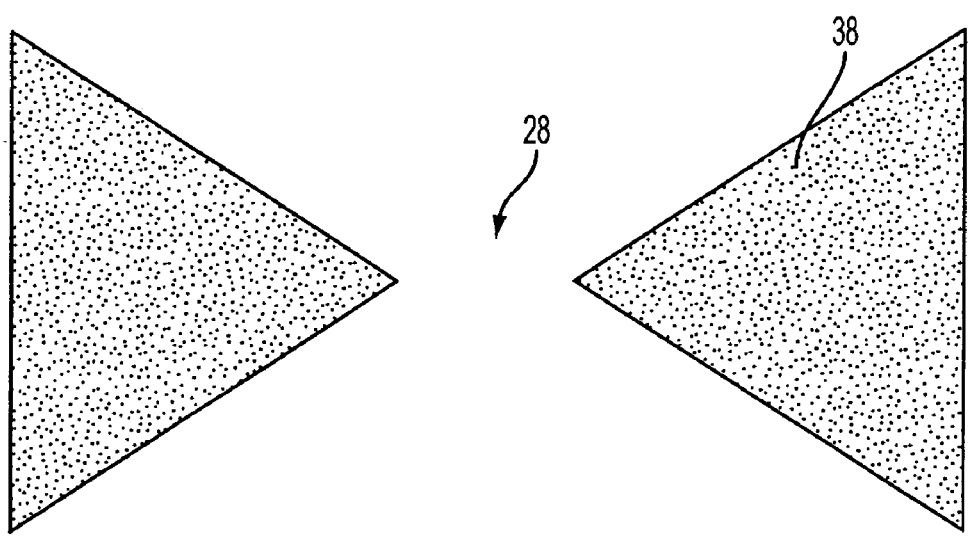
FIG. 7 is a schematic cross-sectional view of a known knife-edge pinhole collimator aperture.
Figure 8:
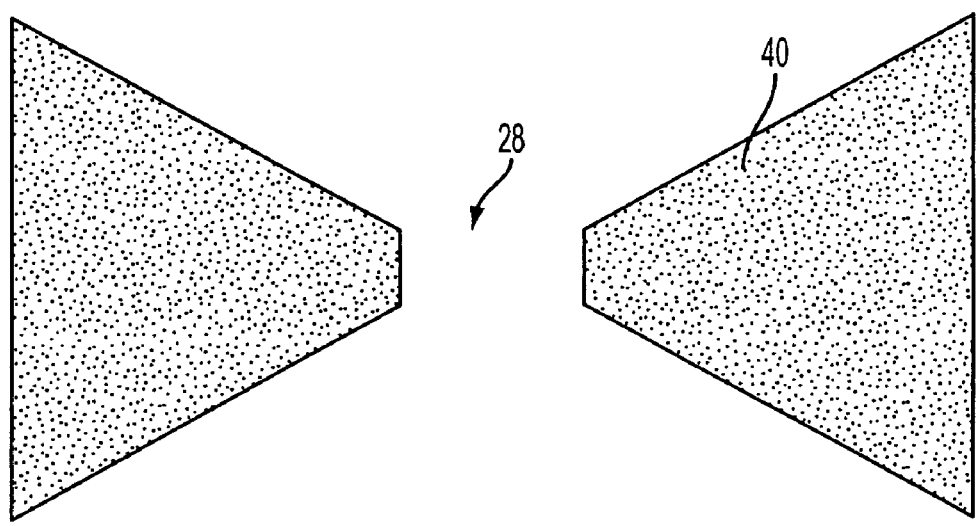
FIG. 8 is a schematic cross-sectional view of a known keel-edge pinhole collimator aperture.

In an aspect of the invention, collimator 24 can include a plurality of pinhole apertures 28 having aperture acceptance angles α, as shown in FIGS. 3 and 4. The acceptance angle can be selected such that each pinhole aperture 28 projects a non-overlapping area of a field of view of test object 20 being imaged onto scintillator 22 of the preclinical nuclear imaging detector system 10 so as to collectively project a unitary minified radiation image of test object 20 onto scintillator 22. In another aspect, alone or in combination with that described above, multi-pinhole collimator 24 can include one or more septa 30, e.g., made of suitable dense material, such as lead or tungsten polymer, etc., positioned between pinhole plate 34 and scintillator 22 and between at least two pinhole apertures 28. For example, FIG. 2 illustrates a preclinical nuclear imaging detector system 10 including septa 30 wherein multiple conical projections 32 do not overlap each other at their point of intersection with scintillator 22. Overlap can be further prevented and/or minimized by adjusting the pinhole acceptance angle α and focal length f without septa 30, as shown in FIGS. 3 and 4, or by adjusting the acceptance angle α and focal length f in addition to providing the septa 30. Pinhole apertures 28 can include a number of types thereof, including but not limited to, knife 38 or keel 40 as disclosed in FIGS. 7 and 8, respectively.

Figure 9A:
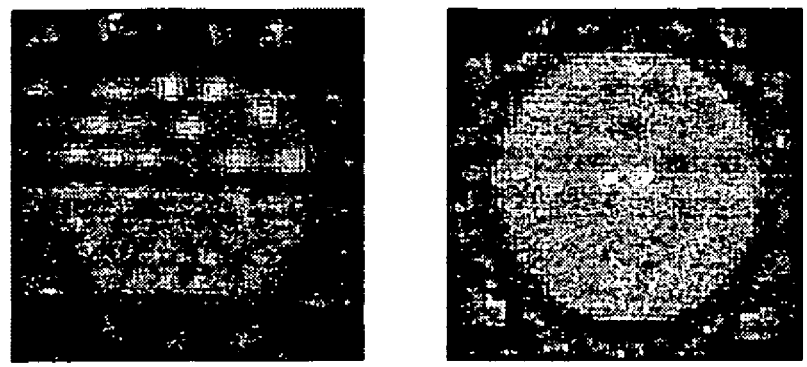
FIG. 9a illustrates images of a phantom using a preclinical nuclear imaging detector system according to the instant invention wherein distance d is 225 mm.
Figure 9B:
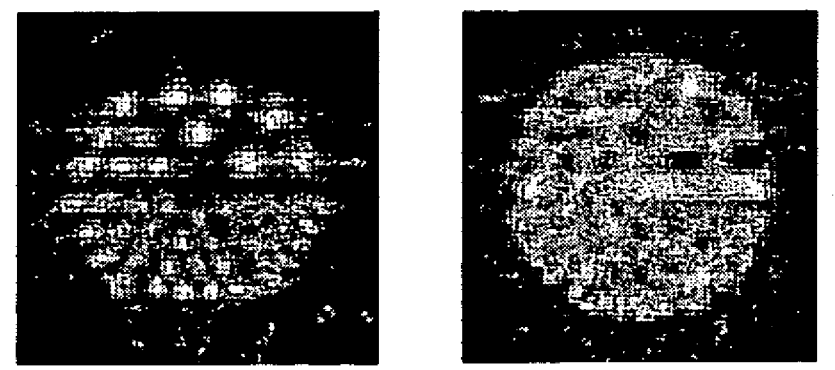
FIG. 9b illustrates images of a phantom using a preclinical nuclear imaging detector system according to the instant invention wherein distance d is 125 mm.

Detector assembly 12 is configured such that the focal length f, between collimator plate 24 and scintillator 22 can be adjusted, as can distance d between object 20 and collimator plate 24. More specifically, FIGS. 3 and 4 illustrate detector assembly 12 wherein pinhole plate 34 is disposed at first and second positions, respectfully, relative to scintillator for purposes of adjusting focal length. As illustrated in FIGS. 3-4 and 6, in exemplary embodiments, distance d between the pinhole plate 34 and object 20 can be between 1 mm to 1 cm, preferably between 100 mm to 300 mm, and more preferably, between 125 mm and 225 mm. FIGS. 9A and 9B illustrate images of a phantom wherein the distance between pinhole plate 34 and object 20 is 225 mm and 125 mm, respectively. Adjustment of focal length f and/or distance d can be accomplished by providing septa 30 and/or collimator sidewalls 36 that are slidable relative to one another, as along tracks or channels, etc. As illustrated in FIG. 5 the septa 30 and/or side walls 36 can include friction reducing element 38, such as wheels, for easing movement therebetween.

Referring now to FIG. 6, a preclinical nuclear imaging detector system according to the instant invention can comprise a plurality of detector assemblies optionally positionally fixed relative to gantry and/or support structure 11 and about axis 14 to describe a perimeter 16. In the embodiment illustrated in FIG. 6, perimeter 16 describes a portion of an ellipse, which ellipse can describe a circle and/or arc. Alternatively, perimeter 16 can describe a portion of a polygon for example, a rectangle, which can further describe a square.

While an imaging device according to the instant invention can be used for obtaining images of a subject, it is preferably configured for use to conduct preclinical assessments on, for example, test objects such as laboratory animals 20. In one embodiment, when the preclinical nuclear imaging detector system according to the instant invention is configured for laboratory animal analyses, the footprint of the system is minimal when compared to known diagnostic SPECT devices used for clinical diagnoses, for example, with human medical patients.

Consequently, a test object 20, such as a laboratory mouse or rat, can be positioned with respect to one or more detector assemblies 12, one or pinhole apertures 28 positioned relative to scintillator 22 to optimize one of spatial resolution and spatial sensitivity and an image of the subject 20 is obtained.

It is understood that while the invention has been described in conjunction with the detailed description thereof, the foregoing description is intended to illustrate and not limit the scope of the invention, which is define by the scope of the appended claims. Other aspects, advantages and modifications are within the scope of the following claims.

What is claimed is:

1. A preclinical nuclear imaging detector system, comprising:
   a gantry and a plurality of detector assemblies, said gantry being fixed and configured for securing said plurality of detector assemblies substantially about an axis to thereby describe a portion of a detector perimeter;
   said plurality of detector assemblies each comprising a scintillator configured to interact with radiation emanating from a test object being imaged, at least one pinhole collimator, having a plurality of pinhole apertures formed therein, said pinhole collimator disposed between said test object and said scintillator, wherein a distance f between the pinhole collimator and the scintillator is selected as a function of the number of pinhole apertures provided in said collimator, such that said plurality of pinhole apertures collectively project a unitary minified radiation image of said target object onto said scintillator; and
   at least one photosensor optically coupled to said scintillator to receive interaction events from said scintillator.

2. The imaging detector system of claim 1 wherein said pinhole collimator apertures comprise a knife-edge pinhole.

3. The imaging detector system of claim 1 wherein said pinhole collimator apertures comprise a keel-edge pinhole.

4. The imaging detector system of claim 1 wherein said perimeter comprises an ellipse.

5. The imaging detector system of claim 1, wherein said perimeter comprises a polygon.

6. The imaging detector system of claim 1, wherein said perimeter comprises a rectangle.

7. The imaging detector system of claim 1, wherein said plurality of detector assemblies further comprises a substantially contiguous array of detectors disposed about said perimeter.

8. The imaging detector system of claim 1, wherein said plurality of detector assemblies comprises an adjustable pinhole plate, said adjustable pinhole plate being adjustably positionable relative to said scintillator and along an axis that is perpendicular to a plane of said scintillator.

9. The imaging detector system of claim 8, wherein said pinhole collimator further comprises a plurality of walls in slidable engagement with one another to allow said pinhole collimator to be adjustably positioned relative to said scintillator.

10. The imaging detector system of claim 1, wherein said collimator comprises a plurality of walls disposed between pinhole apertures and being slidable with respect to one another.

11. The imaging detector system of claim 10, wherein said walls include a friction reducing element therebetween.

12. A method of performing a preclinical scan of a test object employing a preclinical nuclear imaging detector system, comprising:
   providing a gantry and a plurality of detector assemblies, said gantry being fixed and configured for securing said plurality of detector assemblies substantially about an axis to thereby describe a portion of a detector perimeter, said plurality of detector assemblies each comprising a scintillator configured to interact with radiation emanating from a target object being imaged, at least one pinhole collimator, having a plurality of pinhole apertures formed therein, said pinhole collimator being disposed between said test object and said scintillator, wherein a distance f between the pinhole collimator and the scintillator is selected as a function of the number of pinhole apertures provided in said collimator, such that said plurality of pinhole apertures collectively project a unitary minified radiation image of said test object onto said scintillator, and one or more photosensors optically coupled to said scintillator to receive interaction events from said scintillator;
   positioning a test object with respect to said plurality of detector assemblies;
   adjustably positioning said pinhole collimator with respect to said scintillator; and
   obtaining image data of said test object.

13. The method of performing a preclinical scan of a test object employing a preclinical nuclear imaging detector system of claim 12, wherein said pinhole collimator is positionable to effect a desired spatial resolution.

14. The method of performing a preclinical scan of a test object employing a preclinical nuclear imaging detector system of claim 12, wherein said pinhole collimator is positionable to effect a desired spatial sensitivity.

15. The method of performing a preclinical scan of a test object employing a preclinical nuclear imaging detector system of claim 12, wherein a plurality of detectors are configured about a portion of a predefined detector perimeter.

16. The method of performing a preclinical scan of a test object employing a preclinical nuclear imaging detector system of claim 12, wherein said collimators include walls that are slidable with respect to each other.

17. The method of performing a preclinical scan of a test object employing a preclinical nuclear imaging detector system of claim 12, wherein a distance f between said pinhole collimator and said object is between 100 mm and 300 mm.

18. The method of performing a preclinical scan of a test object employing a preclinical nuclear imaging detector system of claim 12, wherein a distance f between said pinhole collimator and said object is between 125 mm and 225 mm.

19. The method of performing a preclinical scan of a test object employing a preclinical nuclear imaging detector system of claim 12, wherein a distance f between said pinhole collimator and said object is 125 mm.

20. The method of performing a preclinical scan of a test object employing a preclinical nuclear imaging detector system of claim 12, wherein a distance f between said pinhole collimator and said object is 225 mm.

* * * * *